United States Patent [19]

Hanson et al.

[11] Patent Number: 4,977,141

[45] Date of Patent: Dec. 11, 1990

[54] PEPTIDYL α-AMINOACYL AMINODIOL CARBAMATES AS ANTI-HYPERTENSIVE AGENTS

[75] Inventors: Gunnar J. Hanson, Skokie; John S. Baran, Winnetaka, both of Ill.

[73] Assignee: G. D. Searle & Co., Chicago, Ill.

[21] Appl. No.: 103,625

[22] Filed: Oct. 1, 1987

[51] Int. Cl.$^5$ .................. A61K 37/02; A61K 37/00; A61K 31/415; C07K 5/00

[52] U.S. Cl. ...................................... 514/19; 530/317; 530/323; 530/328; 530/329; 530/330; 530/331; 530/332; 514/11; 514/400; 514/18; 514/15; 514/16; 514/17; 564/153; 540/482; 540/483; 540/467; 540/470; 540/604; 540/608; 540/544; 540/553; 540/575; 546/245; 546/215; 546/221; 546/226; 546/242; 544/54; 544/58.4; 544/88; 544/97; 544/163; 544/168; 544/316; 544/319; 544/334; 544/335; 544/384; 544/389; 548/531; 548/215; 548/188; 548/201; 548/228; 548/230; 548/300; 548/320; 548/952; 548/953; 548/951; 260/998.2

[58] Field of Search ............... 530/317, 323, 328, 329, 530/330, 331, 332; 514/11, 400, 18, 19, 15, 16, 17; 564/153; 540/482, 483, 467, 470, 604, 608, 544, 553, 575; 546/245, 215, 221, 226, 242; 544/54, 58.4, 88, 97, 163, 168, 316, 319, 334, 335, 384, 389; 548/531, 215, 188, 201, 228, 230, 300, 320, 952, 953, 951; 260/998.2

[56] References Cited

U.S. PATENT DOCUMENTS 4,743,585  5/1988  Hudspeth et al. .................... 514/17

FOREIGN PATENT DOCUMENTS

| 128762 | 12/1984 | European Pat. Off. | 530/317 |
| 172346A | 2/1986 | European Pat. Off. | 530/317 |
| 172347A | 2/1986 | European Pat. Off. | 530/317 |
| 181110 | 5/1986 | European Pat. Off. | 530/317 |
| 189203 | 7/1986 | European Pat. Off. | 530/317 |
| 200406 | 12/1986 | European Pat. Off. | 530/317 |

OTHER PUBLICATIONS

Tsuruo, et al., Japanese Journal Cancer Research, 77, 682–692, Jul. 1986.
Shinoda, et al., Cancer Research, 49, 1722–1726, Apr. 1, 1989.
Burger, Medicinal Chemistry, Interscience Pub., Inc., New York, (1960), pp. 565–571, 579–581, & 600–601.
Matsushita et al, J. Antibiotics 28 1016–1018 (1975).
Lazar et al, Biochem. Pharma. 23 1776–2778 (1974).
Miller et al, Biochem. Pharma. 21 2941–2944 (1972).
Haber, Clinical Sciences 59 7s–19s (1980).
Rich et al, J. Org. Chem. 43 3624 (1978).
Rich et al, J. Med. Chem. 23 27 (1980).
Haber, Clin. and Exper. Hyper. A5(7 & 8) 1193 (1983).
Umezawa et al., J. Antibiot. (Tokyo) 23:259–262 (1970).
Gross et al., Science 175: 656 (1971).
Boger et al., Nature 303 81 (1983).
Kokubu et al., Biochem. Biophys. Res. Commun. 118 929 (1984).
Castro et al, FEBS Lett. 167 273 (1984).
Hanson et al., Biochem. Biophys. Res. Comm. 132 155–161 (1985).
Hanson et al., Biochem. Biophys. Res. Comm. 146 959–963 (1985).
Marshall, Federation Proc. 35 2494–2501 (1976).
Burton et al., Proc. Natl. Acad. Sci. USA 77 5476–5479 (1980).
Suketa et al., Biochemistry 14 3188 (1975).
Swales, Pharm. Ther. 7 173–201 (1979).
Kokubu et al., Nature 217 456–457 (1968).

Primary Examiner—John M. Ford
Assistant Examiner—Robert C. Whittenbaugh
Attorney, Agent, or Firm—J. Timothy Keane; Paul D. Matukaitis

[57] ABSTRACT

Non-peptidyl compounds characterized generally as aminoacyl aminodiol carbamates are useful as renin inhibitors for the treatment of hypertension.

12 Claims, No Drawings

PEPTIDYL α-AMINOACYL AMINODIOL CARBAMATES AS ANTI-HYPERTENSIVE AGENTS

FIELD OF THE INVENTION

Renin-inhibiting compounds are known for control of hypertension. Of particular interest herein are non-peptidyl compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to Produce the octapeptide known as angiotensin II. Angiotensin II is a potent pressor agent responsible for vasoconstriction and elevation of cardiovascular Pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al., in *J. Antibiot.* (Tokyo), 23:259–262 (1970)]. This peptide, known as pepstatin, was found to reduce blood pressure in vivo after the injection of hog renin into nephrectomized rats [Gross et al., *Science,* 175, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger, et al., *Nature*, 303, 81 (1983)]; high molecular weight peptides are generally considered undesirable as drugs because gastrointestinal absorption is impaired and plasma stability is compromised.

Short peptide aldehydes have been reported as renin inhibitors [Kokubu et al., *Biochim. Biophys. Res. Commun.,* 118, 929 (1984); Castro et al., *FEBS Lett.,* 167, 273 (1984)]. Such compounds have a reactive C-terminal aldehyde group and would likely be unstable in vivo.

Other peptidyl compounds have been described as renin inhibitors. EP Appl. No. 128,762, published Dec. 18, 1984, describes dipeptide and tripeptide glycol-containing compounds as renin inhibitors [also see Hanson et al., *Biochem. Biophys. Res. Comm.,* 132:155–161 (1985), 146:959–963 (1987)]. EP Appl. No. 181,110, published May 14, 1986, describes dipeptide histidine derivatives as renin inhibitors EP Appl No. 189,203, published July 30, 1986, describes peptidylaminodiols as renin inhibitors. EP Appl. No. 200,406, published Dec. 10, 1986, describes alkyl naphthylmethyl propionyl-histidyl aminohydroxy alkanoates as renin inhibitors.

For other articles describing previous efforts to devise renin inhibitors, see Marshall, *Federation Proc.,* 35:2494–2501 (1976); Burton et al., *Proc. Natl. Acad. Sci. USA,* 77: 5476–5479 (1980); Suketa et al., *Biochemistry,* 14: 3188 (1975;) Swales, *Parmac. Ther.,* 7: 173–201 (1979); Kokubu et al., *Nature,* 217: 456–457 (1986); Matsushita et al. *J. Antibiotics,* 28: 1016–1018 (1975); Lazar et al., *Biochem. Pharma.,* 23: 2776–2778 (1974); Miller et al., *Biochem. Pharma.,* 21: 2941–2944 (1972); Haber, *Clinical Science,* 59: 7s–19s (1980); Rich et al., *J. Org. Chem.,* 43: 3624 (1978); *J. Med. Chem.,* 23: 27 (1980); especially Haber, *Clin. and Exper. Hyper.,* A5(7&8), 1193 (1983); and European Patent Application Nos. 172346A and 172347A published Feb. 26, 1986.

DESCRIPTION OF THE INVENTION

Non-peptidyl α-aminoacyl aminodiol carbamate compounds having utility as renin inhibitors for treatment of hypertension in mammals constitute a family of compounds of general Formula I:

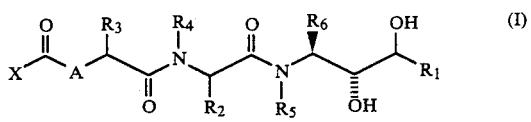

wherein X is selected from

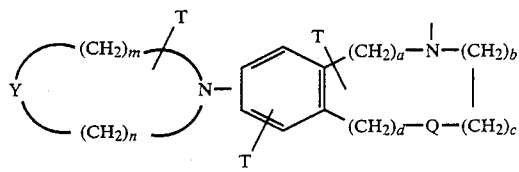

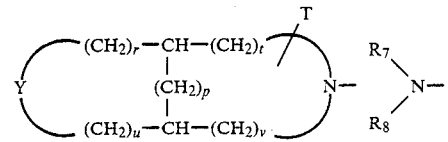

wherein Y and Q are selected from $CH_2$,

O, S, SO, $SO_2$ and $NR_{10}$, wherein $R_9$ is H or lower alkyl, $R_{10}$ is selected from H, phenyl and

and wherein $R_{11}$ is H or lower alkyl; wherein each of m and n is independently an integer from 1 through 4; wherein each of r, t, u and v is independently an integer from zero through 2; wherein p is an integer from 1 through 3; wherein each of a through d is independently an integer from zero through 3; wherein T is selected from one or more groups selected from H, linear or branched lower alkyl, alkoxy, oxo, halo, haloalkyl, lower alkenyl, lower alkynyl and cyano; wherein A is selected from O and S; wherein $R_1$ is selected from H, linear or branched lower alkyl, haloalkyl, alkylcycloalkyl, alkylcycloalkenyl and alkoxycarbonyl; wherein $R_2$ is selected from linear or branched lower alkyl and benzyl; wherein $R_3$ is selected from lower alkyl, acylaminoalkyl, benzyl, naphthylmethyl, aryl and benzyl substituted at the phenyl portion by halo or lower alkyl or by both; wherein each of $R_4$ and $R_5$ is independently selected from H and lower alkyl; wherein $R_6$ is selected from substituted or unsubstituted cycloalkyl, phenyl, cycloalkylalkyl and phenylalkyl, any one of which may be substituted with one or more groups selected from alkyl, alkoxy, halo, haloalkyl, lower alkenyl, lower alkynyl and cyano; and wherein each of $R_7$ and $R_8$ is independently selected from the groups H, lower alkyl, alkenyl, alkynyl, cycloalkyl, phenyl, benzyl, naphthyl and naphthylmethyl, any one of which groups having a substitutable position may be optionally substituted with or more of lower alkyl, alkoxy, alkenyl, alkynyl, halo, haloalkyl, cyano and phenyl, with the proviso that at least one of $R_7$ and $R_8$ is an aryl group.

A preferred group of compounds within Formula I are those compounds having the specific stereochemical configuration shown in Formula II:

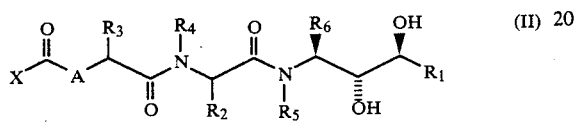

(II)

Preferred compounds within Formula II are those compounds wherein Y and Q are selected from O, $CH_2$, S, $NR_{10}$ wherein $R_{10}$ is H or $$\overset{O}{\underset{}{\overset{\|}{C}R_{11}}}$$

wherein $R_{11}$ is H or lower alkyl; wherein each of m and n is independently an integer from 1 through 3; m, n, v and t is independently zero or one; wherein each of r, t, u and v is independently zero or one; wherein p is one or two; wherein each of a through d is independently an integer from zero through 2; wherein T is selected from one or more groups selected from H, lower alkyl, oxo and halo; wherein A is selected from O and S; wherein $R_1$ is selected from H, lower alkyl, alkylcycloalkyl and alkoxycarbonyl; wherein $R_2$ is selected from lower alkyl and benzyl; wherein $R_3$ is selected from lower alkyl, acylaminoalkyl, benzyl, napthylmethyl, aryl and benzyl substituted at the phenyl portion by halo or lower alkyl or by both; wherein $R_4$ is selected from H and lower alkyl; wherein $R_5$ is H; wherein $R_6$ is selected from cyclohexylmethyl and benzyl; wherein each of $R_7$ and $R_8$ is independently selected from H, phenyl, naphthyl and phenyl substituted with one or more lower alkyl, alkoxy, alkenyl, halo, cyano and phenyl, with the proviso that at least one of $R_7$ and $R_8$ is phenyl.

Within the aforementioned preferred group of compounds, there are four sub-groups of preferred compounds. The first sub-group consists of those compounds of Formula II wherein X is

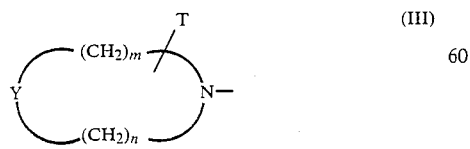

(III)

wherein Y is O or $CCH_2$; m is 2; n is 2; T is one or more of H or lower alkyl; A is O or S; $R_1$ is H or methyl; or lower alkyl; $R_2$ is lower alkyl; $R_3$ is benzyl; $R_4$ is H or methyl; $R_5$ is H or methyl; and $R_6$ is cyclohexylmethyl.

Of this first sub-group the most preferred are those compounds wherein Y is O; m is 2; r is 2; T is one or more of H or methyl; $R_1$ is selected from H, methyl, ethyl and isobutyl; $R_2$ is isobutyl; $R_3$ is selected from benzyl and napthylmethyl $R_4$ is H or methyl; $R_5$ is H or methyl; and $R_6$ is cyclohexylmethyl. Radicals which exemplify the X substituent of Formula III are as follows:

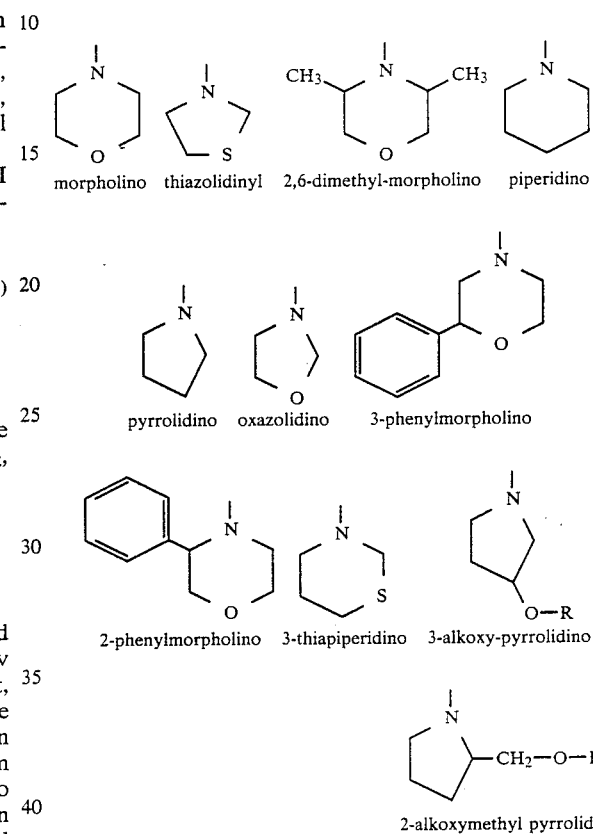

Examples of specific compounds within this sub-group are the following:

O-(N-morpholinocarbonyl)-3-L-phenyllactyl-L-leucinamide of (2S,3R,4S)-2-amino-1-cyclohexyl-3,4-dihydroxy- 6-methylheptane; O-(N-morpholinocarbonyl)-3-L-phenyllactyl-L-leucinamide of (2S,3R,4S)-2-amino-1-cyclohexyl-3,4-dihydroxypentane; and O-(N-morpholinocarbonyl)-3-L-phenyl-lactyl-L-leucinamide of (2S,3R,4S)-2-amino-1-cyclohexyl- 3,4-dihydroxybutane.

A second sub-group of preferred compounds consists of those within Formula I wherein X is

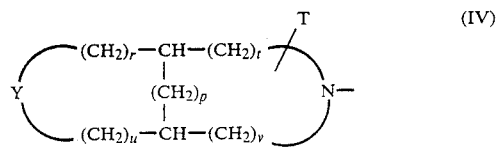

(IV)

wherein Y is selected from O, S, SO, $CH_2$ and $SO_2$; wherein each of r, t, u and v is independently zero or one; r is 2; p is 1 or 2; T is one or more of H, lower alkyl and alkoxy; A is O; $R_1$ is lower alkyl; $R_2$ is lower alkyl; $R_3$ is benzyl $R_4$ is H or methyl; $R_5$ is H or methyl; and $R_6$ is cyclohexylmethyl. The substituent T of Formula IV may be substituted at any substitutable position within the bicyclic structure of Formula IV. Radicals which exemplify the X substituent of Formula IV are as follows:

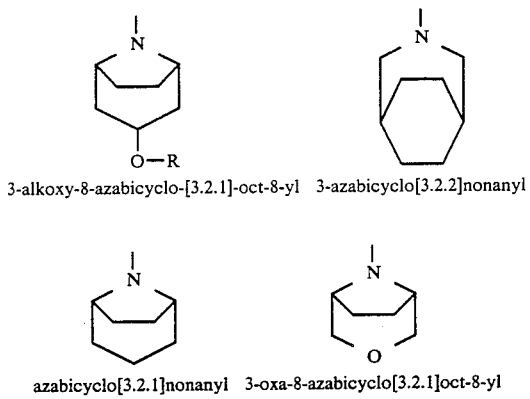

3-alkoxy-8-azabicyclo-[3.2.1]-oct-8-yl    3-azabicyclo[3.2.2]nonanyl azabicyclo[3.2.1]nonanyl    3-oxa-8-azabicyclo[3.2.1]oct-8-yl An example of a compound within this second sub-group is

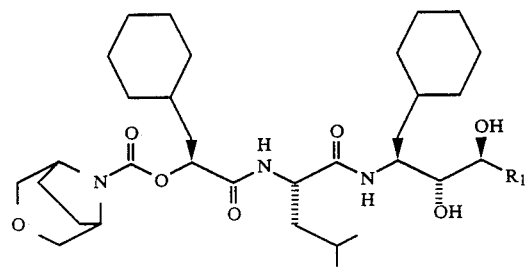

A third sub-group of preferred compounds consists of those compounds wherein X is

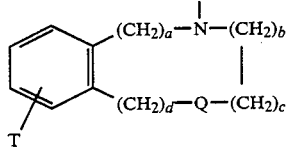

(V)

wherein Q is O or S or $CCH_2$; a is zero; b is 1; c is 1; d is zero; each T is independently one or more of H or lower alkyl; A is O; $R_1$ is selected from H and lower alkyl; $R_2$ is lower alkyl; $R_3$ is benzyl $R_4$ is H or methyl; $R_5$ is H; and $R_6$ is cyclohexylmethyl. Within this third sub-group is a set of more preferred compounds of Formula II wherein Q is O, $R_1$ is selected from H, methyl, ethyl and isobutyl, and $R_2$ is isobutyl, an example of which is a compound wherein $R_1$ is isobutyl, and $R_6$ is cyclohexylmethyl. Another set of more preferred compounds within this third sub-group are those wherein Q is S, $R_1$ is selected from H, methyl and isobutyl, and $R_2$ is isobutyl, an example of which is a compound wherein $R_1$ is isobutyl, and $R_6$ is cyclohexylmethyl. Radicals which exemplify the substituent of Formula V are as follows:

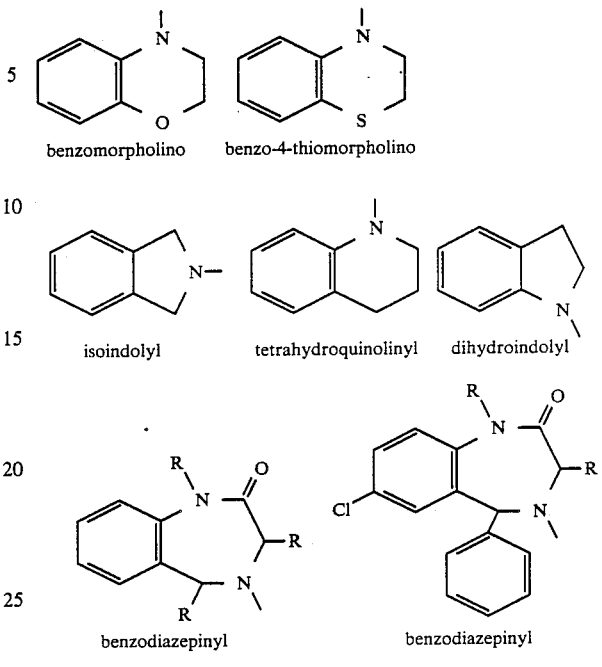

benzomorpholino    benzo-4-thiomorpholino isoindolyl    tetrahydroquinolinyl    dihydroindolyl benzodiazepinyl    benzodiazepinyl Within any of these radicals exemplifying Formulae III, IV and V, the substituent R represents a linear or branched alkyl group of one to about ten carbon atoms, or preferably, one to about five carbon atoms.

A fourth sub-group of preferred compounds consists of those compounds of Formula II wherein X is

(VI)

wherein each of $R_7$ and $R_8$ is independently selected from the groups H, lower alkyl, cycloalkyl, phenyl, benzyl, naphthyl, and naphthylmethyl, any one of which groups having a substitutable position may be optionally substituted with or more of lower alkyl, alkoxy, alkenyl, alkynyl, halo, haloalkyl, cyano and phenyl, with the proviso that at least one of $R_7$ and $R_8$ is an aryl group.

Of this fourth subgroup, more preferred compounds are those wherein A is O, $R_1$ is isobutyl, $R_2$ is isobutyl, $R_3$ is benzyl $R_4$ is H or methyl, $R_5$ is H or methyl, $R_6$ is cyclohexymethyl, and each of $R_7$ and $R_8$ is independently selected from, H, lower alkyl and phenyl, with at least one of $R_7$ and $R_8$ being phenyl. An especially preferred compound is wherein $R_7$ is H and $R_8$ is phenyl. $R_3$ is benzyl $R_4$ is H or methyl, $R_5$ is H or methyl, $R_6$ is cyclohexymethyl, and each of $R_7$ and $R_8$ is independently selected from, H, lower alkyl and phenyl, with at least one of $R_7$ and $R_8$ being phenyl. An especially preferred compound is wherein $R_7$ is H and $R_8$ is phenyl.

Unless otherwise described, the chemical groups recited herein shall have meanings as follows: "Lower alkyl" means alkyl radicals containing one to about 10 carbon atoms in a linear or branched configuration, examples of which include methyl, ethyl, n-propyl, isopropyl, n-butyl, sec-butyl, iso-butyl, tert-butyl, n-pentyl, neopentyl, n-hexyl, 1-methylhexyl, n-heptyl, 2-ethylheptyl, n-octyl, 3-propyloctyl, n-nonyl, 4-butylnonyl, n-decyl and the like. "Lower alkenyl" and "lower alkynyl" mean, respectively, hydrocarbon radicals of two to about ten carbon atoms containing at least one carbon-carbon double bond and at least one carbon-carbon triple bond, respectively, attached to alkyl radicals of the type embraced by the term "lower alkyl" examples of which are 2-butenyl and 2-pentynyl. "Haloalkyl" means alkyl radicals substituted at one or more substitutable positions with one or more halo groups. Preferred haloalkyl group are those provided by lower alkyl radicals substituted at least at one position with one, two or three halo groups such as fluoro or chloro, a specific example of which is trifluoromethyl. "Alkylcycloalkyl" means a cyclized alkyl having from four to about nine ring carbon atoms, any one or more of the substitutable ring carbons being substituted with an alkyl group, preferably a lower alkyl group. "Alkylcycloalkenyl" means a cyclized hydrocarbon radical containing four to about nine ring carbon atoms containing at least one carbon-carbon double bond, but less than the number of double bonds required to form a fully unsaturated ring system, any one or more of the substitutable ring carbon atoms being substituted with an alkyl group, preferably a lower alkyl group. "Alkoxycarbonyl" means an oxycarbonyl radical having an alkyl, preferably lower alkyl, group attached to the oxygen atom. "Aryl" means an aromatic hydrocarbon radical provided by a homocyclic or heterocyclic ring system, such as phenyl, naphthyl, and pyridyl. "Acyl" means a carbonyl radical attached to a hydrocarbon moiety, typically an alkyl or lower alkyl group.

Based upon the foregoing, the meanings of the following terms should be readily discernible, namely, "acylaminoalkyl", "cycloalkyl", "cycloalkylalkyl", "phenylalkyl" and "alkoxy".

In the cyclic structures of Formulae III, IV and V where the substituent T is shown, it is intended that the T substituent represents one or more substituents which may be attached at any substitutable position on any of the described cyclic structures.

Compounds of Formula I may have two or more carbon atoms providing asymmetric sites which are important for conferring activity. Preferred compounds have three asymmetric carbons which tend to confer improved activity. Such compounds whether in their pure isomer form or as diastereomeric mixtures are embraced in the Formula I and II compounds, of the invention. Many of the more active renin inhibitors are provided by compounds having a specific stereochemical configuration. Within Formula I, reading from the N terminus to the C terminus (terminating with the diol moiety), the preferred configurations for the asymmetric carbons are as follows: S,S,S,R,S.

Compounds of Formula I have been found to inhibit the production of angiotensin II in mammals. Angiotensin II is a potent vasoconstrictor and participates in the formation of aldosterone which regulates sodium and water balance in mammals Thus, compounds of Formula I are therapeutically useful in methods for treating hypertension by administering to a hypertensive patient a therapeutically-effective amount of a compound of Formula I.

These compounds can be formulated into pharmaceutically-acceptable dosage forms by any of a number of well-known carriers or diluents. The compounds can be formulated using pharmacologically-acceptable acid addition salts and can be used in a suitable hydrated form. The formulated compounds can be administered in oral dosage forms such as tablets, capsules, pills, powders, or granules. The compounds can also be administered intramuscularly, using forms known to the pharmaCeutical art. In general, the preferred form of administration is oral. A therapeutically effective but non-toxic quantity of the compound is employed in treatment of high blood pressure in mammals. The dosage regimen for preventing or treating hypertension with the compounds of Formula I is selected upon consideration of a variety of factors, including the type, age, weight, sex, and medical condition of the patient, the severity of the hypertension, the route of administration, and the particular compound employed. Dosages of the compounds are ordinarily in the range from about 0.5 to about 100 mg/kg (active compound-to-body weight), and preferably from about 1.0 to about 20 mg/kg given orally or by injection.

Compounds of Formula I are also useful as diagnostic agents for identification of hypertension due to renin excess.

Compounds of Formula I can be administered as prodrugs. Preferably, esterification of one or more of the hydroxyl groups of the compounds of Formula I is accomplished with amino acids to make aminoesters, succinates to make succinic acid esters, or phosphates to make phosphoric acid esters. Aminoesters of the Formula I compounds are more preferred.

Procedures for preparation of compounds of Formula I ar set forth in the schemes and descriptions under Generic Synthesis I and Generic Synthesis II, taken with the specific procedures described in Examples 1-13 which follow thereafter. The substituents A, X and $R_1$ through $R_6$ are as described above for the Formula I substituents.

Generic Synthesis Schemes I & II

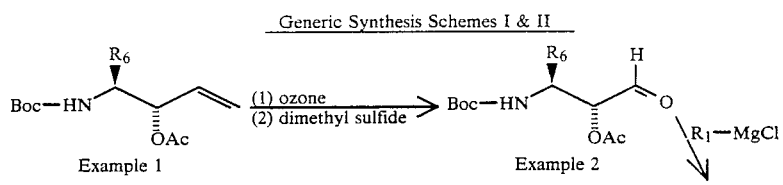

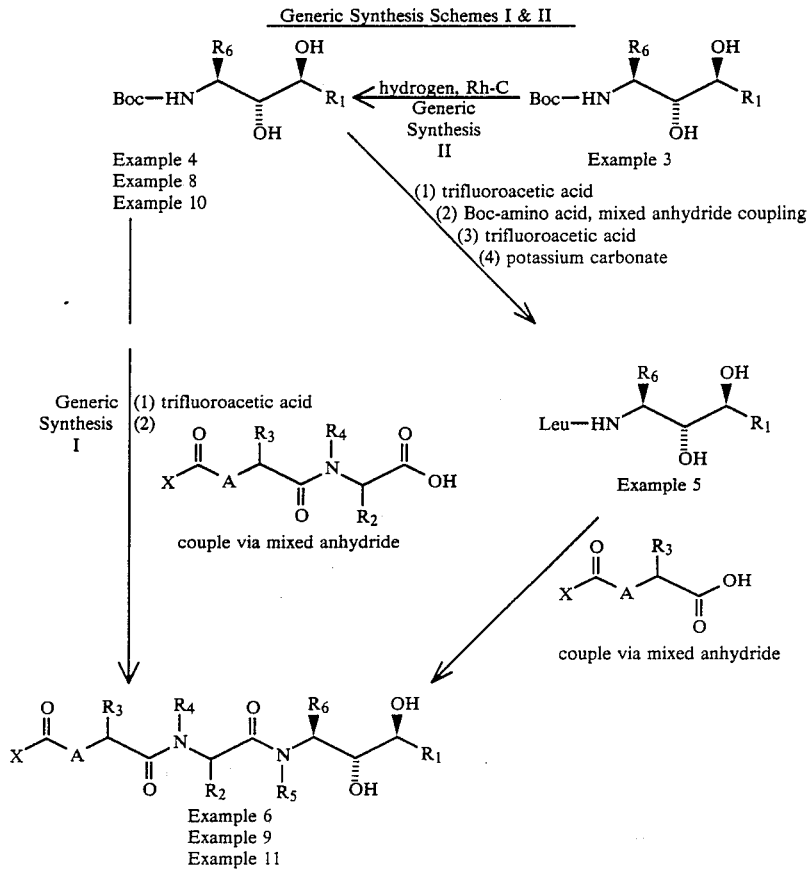

Generic Synthetic Description I

An allylic acetate, appropriately substituted and suitably protected, as shown in the scheme is used as starting material This substance, and like substances, are ozonized under standard conditions (low temperature, as methanol-methylene chloride solutions) and the reduction of the ozonide to an aldehyde is effected with dimethyl sulfide. Once obtained, this type of aldehyde is treated with organometallic reagents capable of delivering an alkyl group to the aldehyde to produce diols of the type shown. These diols may then be converted, using standard peptide coupling methodology to renin inhibitors as shown via coupling to the general acid shown in the scheme. The initially obtained diol may also be hydrogenated to the saturated cyclohexane diol and again, coupled to in a similar manner to acids of the general description given in the scheme.

General Synthetic Description II

Diols are obtained as before, but using this method, stepwise coupling is carried out, using standard methodology developed for peptide synthesis, to obtain the renin inhibitors depicted in the scheme.

The following Synthetic Scheme is a more specific description of the preceeding Generic Synthesis Outlines I and II. This Synthetic Scheme outlines preparations of the specific compounds of Examples 1–13, which follow.

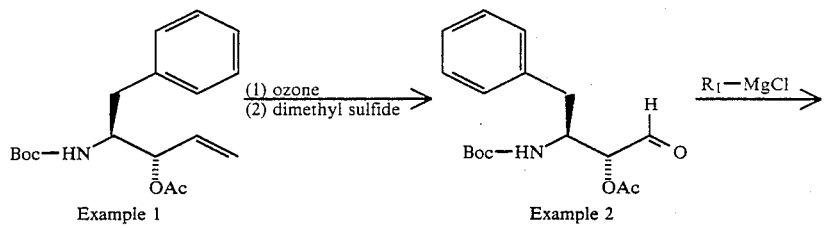

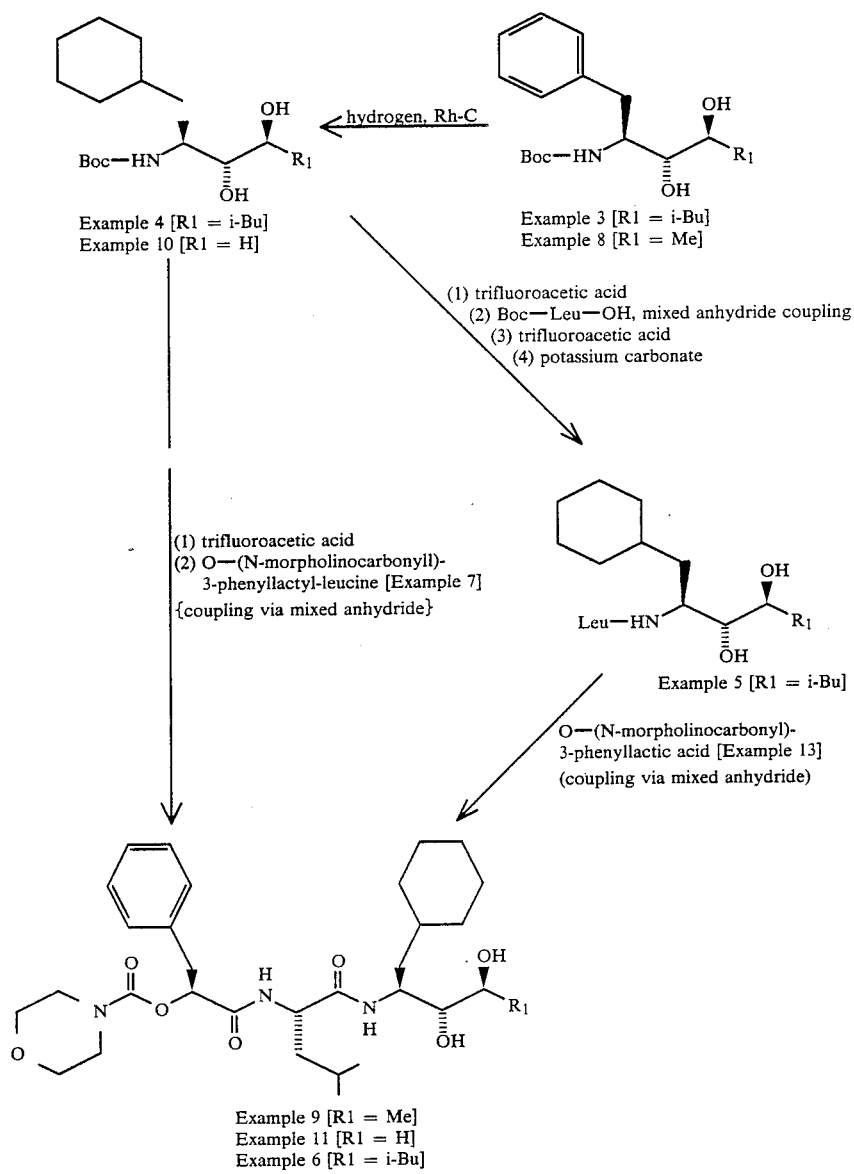

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees Centigrade. Within the foregoing synthetic description and examples which follow, abbreviations have meanings as indicated below:

BOC butyloxycarbonyl
i-Bu=isobutyl
Leu=leucine
Ac=acyl
Mc=methyl
TFA=trifluoroacetic acid
THR=tetrahydrofuran

EXAMPLE 1

(3S,4S)-N-[(tert-Butyloxy)carbonyl]-4-amino-3-acetoxy-5-phenylpenten

The preparation of the above intermediate was carried out using the procedure described in Hanson, et al., (1985) J. Org. Chem. 50,5399.

EXAMPLE 2

(2R,3S)-N-[(tert-Butyloxy)carbonyl]-3-amino-2-acetoxy-4-phenylbutanal

The preparation of the above intermediate was carried out as described in Hanson, et al. above. Ozone/oxygen was bubbled at −70° into a solution of 2.55 g (8.0 mmol) of the allylic acetate of Example 1 in 100 mL of methylene chloride until a deep blue color persisted. Oxygen was introduced until the blue color completely faded, then 3.0 mL of Me₂S was added and the solution was allowed to warm to 0°-5° and stand overnight. The solvent was removed at 0° under vacuum yielding the title compound as a thick yellow oil which was used in the following step without purification.

EXAMPLE 3

(2S,3R,4S)-N-[(tert-Butyloxy)carbonyl]-2-amino-1-phenyl-3,4-dihydroxy-6-methylheptane The oil prepared in Example 2 was dissolved under nitrogen in 100 mL of dry THF and cooled to −70°. To this solution was added 13 mL (26 mmol) of a 2.0 M solution of isobutylmagnesium chloride in ether and the stirred mixture was allowed to warm to room temperature and stir for 2 hrs. After decomposition with MeOH/H$_2$O the mixture was diluted with ether, washed with saturated NH$_4$Cl solution twice, then dried and the solvents stripped off under vacuum. The residue was allowed to stand overnight in 80% MeOH—H$_2$O containing excess ammonium hydroxide. The MeOH was stripped off and the mixture was extracted with ether. These extracts were combined, washed with water, dilute KHSO$_4$, then dried and evaporated to give 2.36 g of a yellow glass which crystallized from 50 mL of pentane on standing overnight. The yellow-white powder obtained was recrystallized from ether-hexane and furnished the title compound (0.41 g) as white, hairy needles, mp 134°–136°, Rf (ether): single spot, 0.6. By chromatography of the mother liquors and crystallization of the appropriate fractions, an additional 0.22 g of product, mp 138°–139° was obtained.

Anal: Calcd. for C$_{19}$H$_{31}$NO$_4$ (337.45): C, 67.62; H, 9.26; N, 4.15. Found: C, 67.51; H, 9.43; N, 4.24.

EXAMPLE 4

(2S,3R,4S)-N-[(tert-Butyloxy)carbonyl]-2-amino-1-cyclohexyl-3,4-dihydroxy-6-methylheptane The diol of Example 3, 0.27 g, was reduced in MeOH with 60 psi H$_2$ at 60° in 3 hrs using 5% Rh/C catalyst. After filtering, the solvent was stripped off and the 0.27 g of white crystals were recrystallized from CH$_2$Cl$_2$-hexane to furnish tiny needles of the title compound, 0.19 g, mp 126°–128°; further recrystallization gave mp 128.5°–129.5° Rf (ether): single spot, 0.8. title calcd. for C$_{19}$H$_{37}$NO$_4$(343.50): C, 66.43; H, 10.86, N, 4.08. Found: C, 66.43; H, 11.01; N, 4.03.

EXAMPLE 5

-L-Leucinamide of (2S,3R,4S)-2-amino-1-cyclohexyl-3,4-dihydroxy-6-methylheptane

The compound of Example 4 was treated with trifluoroacetic acid (TFA) to remove the Boc group and this amine was then coupled to the mixed carbonic anhydride formed from isobutylchloroformate and Boc-L-leucine-OH following the general procedure given in Example 6. This amide was treated with TFA and the resulting salt was neutralized with potassium carbonate-water solution to produce the title free base: Rf=0.45 (single spot, 9:1 methylene chloride-MeOH, silica); 400 MHz NMR (DMSO) spectrum: consistent with structure.

EXAMPLE 6

O-(N-morpholinocarbonyl)-3-L-phenyllactyl-L-leucinamide of (2S,3R,4S)-2-amino-1-cyclohexyl-3,4-dihydroxy-6-methylheptane O-(N-morpholinocarbonyl)-3-L-phenyllactic acid (104 mg), prepared in Example 13, dissolved in 0.75 mL of methylene chloride was cooled to −10° and N-methyl piperidine (35 mg) was added, followed by isobutylchloroformate (44 mg); after stirring this solution for 5 min, a slurry of the title free amine of Example 5 (70 mg) in 1 mL of methylene chloride was added. This mixture was allowed to stand at 0° for 8 h, then the solvent was evaporated and the residue taken up in methanol. 1 N potassium hydroxide solution (0.5 mL) was added and the solution was allowed to stand at room temperature for 2 min, whereupon 0.5 M citric acid was added. The mixture was extracted with ethyl acetate and the organic layer was washed with 5% potassium carbonate, followed by water and brine and then dried over sodium sulfate. The solvent was evaporated to give the title compound as a solid (120 mg, 99% yield): 400 MHz NMR (CDCl$_3$): consistent with structure; HPLC analysis showed a single peak.

Anal. calcd for C$_{34}$H$_{55}$N$_3$O$_7$+0.5 H$_2$O: C, 65.14; H, 9.00; N, 6.70.

Found: C, 65.17; H, 8.83; N, 6.41

EXAMPLE 7

O-(N-morpholinocarbonyl)-3-L-phenyllactyl-L-leucine

This intermediate was made using the procedure above for the preparation the title compound of Example 6 except that leucine methyl ester was substituted for the title compound of Example 5. The resulting ester was saponified with sodium hydroxide-water to produce the title acid: 80 MHz NMR (CDCl$_3$):.. consistent with structure.

Anal. calcd for C$_{20}$H$_{28}$N$_2$O$_6$: C, 61.37; H, 7.16; N, 7.15.

Found: C, 61.29; H, 7.33; N, 7.03

EXAMPLE 8

(2S,3R,4S)-N-Boc-2-amino-1-cyclohexyl-3,4-dihydroxypentane

The procedure of Example 3 followed by that of Example 4 was employed, substituting methylmagnesium bromide for isobutylmagnesium chloride to give the title compound:

Anal. calcd for C$_{16}$H$_{31}$NO$_4$: C, 63.75; H, 10.37; N, 4.65. Found: C, 63.63; H, 10.55; N, 4.65.

EXAMPLE 9

O-(N-morpholinocarbonyl)-3-L-phenyllactyl-L-leucinamide of (2S,3R,4S)-2-amino-1-cyclohexyl-3,4-dihydroxypentane (2S,3R,4S)-N-Boc-2-amino-1-cyclohexyl-3,4-dihydroxypentane (described in Example 8) was treated with TFA and then the resulting salt was coupled to the free acid of Example 7 using the coupling procedure of Example 6 to produce the title renin inhibitor:

Anal. calcd for C$_{31}$H$_{49}$N$_3$O$_7$: C, 64.67; H, 8.57; N, 7.29. Found: C, 64.71; H, 8.87; N, 6.98.

EXAMPLE 10

(2S,3R)-N-Boc-2-amino-1-cyclohexyl-3,4-dihydroxybutane

The procedure of Example 4 was employed using (2S,3R)-N-Boc-2-amino-1-phenyl-3,4-dihydroxybutane, prepared by the method of Hanson, et al., to give crystalline title compound:

Anal. calcd for $C_{15}H_{29}NO_4$: C, 62.69; H, 10.17; N, 4.87. Found: C, 62.69; H, 10.51; N, 4.91.

EXAMPLE 11

O-(N-morpholinocarbonyl)-3-L-phenyllactyl-L-leucinamide of (2S, 3R)-2-amino-1-cyclohexyl-3,4-dihydroxybutane (2S,3R)-N-Boc-2-amino-1-cyclohexyl-3,4-dihydroxybutane (described in Example 10) was treated with TFA and then the resulting salt was coupled to the free acid of Example 7 using the coupling procedure of Example 6 to product the title renin inhibitor:

Anal. calcd for $C_{30}H_{47}N_3O_7$: C, 64.15; H, 8.43; N, 7.47. Found: C, 63.97; H, 8.52; N, 7.22.

EXAMPLE 12

Methyl L-3-phenyllactate

L-3-Phenyllactic acid (5 g, 30 mmol) was dissolved in 25 mL of dimethylformamide and cesium carbonate (9.94 g, 30.5 mmol) was added. After the evolution of gas ceased, methyl iodide (8.52 g, 60 mmol) was added and the mixture was stirred for 18 hours at room temperature. Water was then added and the mixture extracted with ethyl acetate. The organic phase was separated, washed with water, dried over magnesium sulfate, and the solvent removed in vacuo to give the title compound as a colorless oil (5.4 g, 100%° yield).

Anal. calcd for $C_{10}H_{12}O_3$: C, 66.65; H, 6.71. Found: C, 66.62; H, 6.69.

EXAMPLE 13

O-(N-morpholinocarbonyl)-3-L-phenyllactic acid

The methyl ester of Example 12 (5 g, 30 mmol) was dissolved in a toluene solution of phosgene (70 mL, 2.5 M). This solution was cooled to 0° and triethylamine (6.1 g, 60 mmol) was added over a 5 min period. The solution was allowed to warm to room temperature and stir for 18 hours. The solvent was removed in vacuo and the residue was extracted with ethyl acetate (200 mL) and filtered. The filtrate was treated with morpholine (10.4 g, 120 mmol) and this mixture was stirred at room temperature for 18 hours. Water was added to dissolve the precipitate and 5% HCl was added to bring the solution to pH 1. The organic phase was separated, washed with water, dried over magnesium sulfate and the solvent evaporated to give a yellow oil (7.42 g). This residue was chromatographed on silica to give a methyl ester (1.3 g). This ester was dissolved in methanol (4.5 mL) and treated with 2 N NaOH (4.4 mL) and the mixture stirred at room temperature for 3 hours. 10% aqueous HCl was added dropwise until no further precipitation occurred. The precipitate was extracted with ethyl acetate, dried over sodium sulfate and the solvent evaporated to give the title compound (1.1 g) as a colorless oil; 300 MHz NMR (CDCl$_3$), consistent with structure.

Biological Evaluation

Compounds of Formula I were evaluated as inhibitors of human renin in an in vitro assay, as follows: This human renin inhibition test has been previously described in detail [Papaioannou, et. al., *Clinical and Experimental Hypertension*, A7(9), 1243–1257 (1985)]. Human renin was obtained from the National Institute for Biological Standards, London. In a total volume of 0.25 mL 100 mM Tris-acetate buffer at PH 7.4, $25 \times 10^{-6}$ Goldblatt units of renin, 0.05 mL of plasma from human volunteers taking oral contraceptives, 6.0 mM sodium EDTA, 2.4 mM phenylmethyl sulfonyl fluoride, 1.5 mM 8-hydroxyquinoline, 0.4 mg/mL BSA, and 0.024 mg/mL neomycin sulfate were incubated for two hours at 37° C. in the presence or absence of renin inhibitors. The produced angiotensin I was determined by radioimmunoassay (New England Nuclear kit). Dipeptide glycols to be assayed were solubilized in either ethyl alcohol or DMSO and diluted with 100 mM Tris-acetate buffer at pH 7.4 to the appropriate concentration. The final concentration of organic solvent in the reaction mixture was less than 1%. Control incubations at 37° C. were used to correct for effects of organic solvent on renin activity.

The hog renin inhibition assay was conducted in a manner similar to the human resin assay, with the following modification: Hog renin was purchased from Sigma Chemical Co. and the synthetic tetradecapeptide substrate was obtained from peninsula Labs Inc. In a final volume of 0.25 mL 100 mM Tris-acetate buffer at pH 7.4, 0.125 m units hog renin, 20 micromolar tetradecapeptide, 6 mM disodium EDTA, 3.2 mM phenylmethyl sulfonyl fluoride, 3 mM 8-hydroxyquinoline, 1.2 mg/mL BSA and 0.024 mg/mL neomycin sulfate were incubated for one hour at 37° C. in the presence or absence of renin inhibitors. The amount of angiotensin I produced was determined as for the human renin inhibition assay.

The effect of inhibitor on plasma renin activity (PRA) in Rhesus monkeys was determined as follows: Rhesus monkeys were pre-treated with furosemide (0.2 mg/kg; i.m.) followed by another equal does 6 hours later. Then, 24 hours after the first treatment, the animals were chaired and blood samples collected for pre-treatment controls; immediately thereafter dosing with drug was started. The compounds were administered intravenously every 30 min and blood samples were collected 15 min after each administration. PRA was determined by the method of Sealey and Laragh *Cardiovascular Med.* 2, 1079–1092 (1977), and the concentration of angiotensin I produced was determined by radioimmunoassay. The dose required to reduce PRA to 50% of the pretreatment control value is given in Table I as the ED$_{50}$. Biological Results:

TABLE I

Effect of Compounds on Renin Activity

| Compound | Human Renin IC$_{50}$ | Hog Renin IC$_{50}$ | Rhesus (in vivo) PRA Reduction ED$_{50}$ |
|---|---|---|---|
| Example 6 | $7 \times 10^{-8}$ M | $1.6 \times 10^{-7}$ M | 0.012 mg/kg |
| Example 9 | $1 \times 10^{-7}$ M | $6.6 \times 10^{-6}$ M | — |
| Example 11 | $4.9 \times 10^{-7}$ M | $7.2 \times 10^{-6}$ M | 1.6 mg/kg |

The oral activity of compounds of Formula I was determined in vivo in Marmoset monkeys in accordance with the following procedure: Common marmosets (Callithrix jacchus, Charles River) were placed on a modified high protein low sodium diet (Purina, St. Louis, Mo.) for 1 to 2 weeks. On the day of the test an animal was anesthetized with isoflurane and cannulated in the femoral artery and vein for blood pressure monitoring, intravenous saralasin infusion and blood sampling. After allowing the animal to recover from surgery for 2 hr, saralasin was infused at 1 microgram/min for 15 minutes to confirm that the animal's blood pressure was dependent on angiotensin II levels. The marmoset was allowed to stabilize for 30 min after the saralasin infusion. The test compound was administered orally and blood pressure was monitored for 2 hr. Blood samples were taken in K-EDTA for plasma renin activity before, 30 min, and 1 hr after compound administration. Results are shown in Table II.

TABLE II

| Plasma Renin Activity of Sodium-Depleted Marmoset | | | | | |
|---|---|---|---|---|---|
| Time of Compound Administration | Example 6 Compound* Animal No. | | | | Example 11 Compound* Animal No. |
| | 206 | 207 | 208 | 209 | 205 | 221 |
| Pretreatment | 16.3 | 16.4 | 15.7 | 39.3 | 17.5 | 37.6 |
| 30 min | 2.2 | 0.2 | 1.0 | 1.1 | 0.6 | 48.5 |
| 60 min | 0.6 | 0.9 | 2.0 | 0.0 | 4.5 | 24.9 |

*20 mg/kg; route: IG Plasma Renin Activity in ng AI/ml/hr

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula:

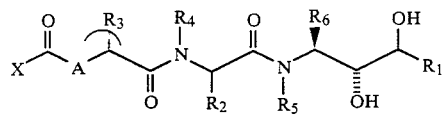

wherein X is 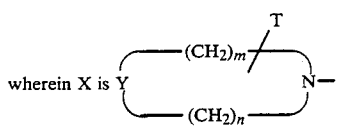

wherein Y is O; m is 2; n is 2; T is one or more of H or methyl; $R_1$ is selected from H, methyl, ethyl and isobutyl; $R_2$ is isobutyl; $R_3$ is selected from benzyl and napthylmethyl; $R_4$ is H or methyl; $R_5$ is H or methyl; and $R_6$ is cyclohexylmethyl; A is O or S or a pharmacologically-acceptable salt thereof.

2. Compound of claim 1 which is O-(N-morpholinocarbonyl)-3-L-phenyllactyl-L-leucinamide of (2S, 3R, 4S)-2-amino-1-cyclohexyl-3,4-dihydroxy-6-methylheptane; or a pharmacologically-acceptable salt thereof.

3. Compound of claim 1 which is O-(N-morpholinocarbonyl)-3-L-phenyllactyl-L-leucinamide of (2S, 3R, 4S)-2-amino-1-cyclohexyl-3,4-dihydroxypentane; or a pharmacologically-acceptable salt thereof.

4. Compound of claim 1 which is O-(N-morpholinocarbonyl)-3-L-phenyllactyl-L-leucinamide of (2S, 3R)-2-amino-1cyclohexyl-3,4-dihydroxybutane; or a pharmacologically-acceptable salt thereof.

5. A pharmaceutical composition comprising a therapeutically-effective amount of a renin-inhibiting compound and a pharmaceutically-acceptable carrier or diluent, said renin-inhibiting compound selected from a family of compounds of the formula:

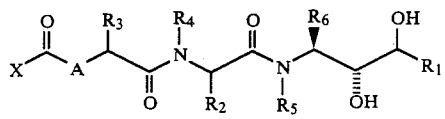

wherein X is 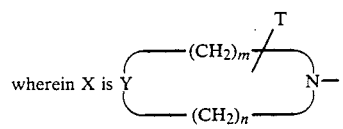

wherein Y is O; m is 2; n is 2; T is one or more of H or methyl; $R_1$ is selected from H, methyl, ethyl and isobutyl; $R_2$ is isobutyl; $R_3$ is selected from benzyl and napthylmethyl; $R_4$ is H or methyl; $R_5$ is H or methyl; and $R_6$ is cyclohexylmethyl; A is O or S or a pharmacologically-acceptable salt thereof.

6. The pharmaceutical composition of claim 5 wherein said renin-inhibiting compound is O-(N-morpholinocarbonyl)-3-L-phenyllactyl-L-leucinamide of (2S, 3R, 4S)-2-amino-1-cyclohexyl-3,4-dihydroxy-6-methylheptane; or a pharmaceutically-acceptable salt thereof.

7. The pharmaceutical composition of claim 5 wherein said renin-inhibiting compound is O-(N-morpholinocarbonyl)-3-L-phenyllactyl-L-leucinamide of (2S, 3R, 4S)-2-amino-1-cyclohexyl-3,4-dihydroxypentane; or a pharmacologically-acceptable salt thereof.

8. The pharmaceutical composition of claim 5 wherein said renin-inhibiting compound is O-(N-morpholinocarbonyl)-3-L-phenyllactyl-L-leucinamide of (2S, 3R)-2-amino-1-cyclohexyl-3,4-dihydroxybutane; or a pharmacologically-acceptable salt thereof.

9. A therapeutic method for treating hypertension, said method comprising administering to a hypertensive patient a therapeutically-effective amount of a compound of the formula:

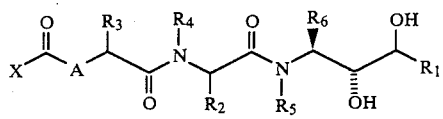

wherein X is 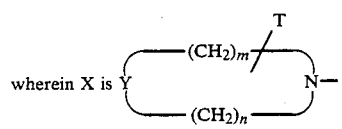

wherein Y is O; m is 2; n is 2; T is one or more of H or methyl; $R_1$ is selected from H, methyl, ethyl and isobutyl; $R_2$ is isobutyl; $R_3$ is selected from benzyl and napthylmethyl; $R_4$ is H or methyl; $R_5$ is H or methyl; and $R_6$ is cyclohexylmethyl; A is O or S or a pharmacologically-acceptable salt thereof.

10. The therapeutic method of claim 9 wherein said compound is O-(N-morpholinocarbonyl)-3-L-phenyllactyl-L-leucinamide of (2S, 3R, 4S)-2-amino-1-cyclohexyl-3,4-dihydroxy-6-methylheptane; or a pharmaceutically-acceptable salt thereof.

11. The therapeutic method of claim 9 wherein said compound is O-(N-morpholinocarbonyl)-3-L-phenyllactyl-L-leucinamide of (2S, 3R, 4S)-2-amino-1- cyclohexyl-3,4-dihydroxypentane; or a pharmacologically-acceptable salt thereof.

12. The therapeutic method of claim 9 wherein said compound is O-(N-morpholinocarbonyl)-3-L-phenyl-lactyl-L-leucinamide of (2S, 3)-2-amino-1-cyclohexyl-3,4-dihydroxybutane; or a pharmacologically-acceptable salt thereof.

* * * * *